US008845999B2

(12) United States Patent
Wright et al.

(10) Patent No.: US 8,845,999 B2
(45) Date of Patent: Sep. 30, 2014

(54) TRACERS FOR MONITORING THE ACTIVITY OF SODIUM/GLUCOSE COTRANSPORTERS IN HEALTH AND DISEASE

(75) Inventors: Ernest M. Wright, Los Angeles, CA (US); Jorge R. Barrio, Agoura Hills, CA (US); Bruce A. Hirayama, Los Angeles, CA (US); Vladimir Kepe, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1580 days.

(21) Appl. No.: 11/920,904

(22) PCT Filed: May 23, 2006

(86) PCT No.: PCT/US2006/020137
§ 371 (c)(1),
(2), (4) Date: Aug. 5, 2009

(87) PCT Pub. No.: WO2006/127842
PCT Pub. Date: Nov. 30, 2006

(65) Prior Publication Data
US 2010/0008856 A1    Jan. 14, 2010

Related U.S. Application Data (60) Provisional application No. 60/683,642, filed on May 23, 2005.

(51) Int. Cl.
*A61K 51/00* (2006.01)
*A61M 36/14* (2006.01)
*G01N 33/60* (2006.01)
*G01N 33/68* (2006.01)

(52) U.S. Cl.
CPC ............ *G01N 33/60* (2013.01); *G01N 33/6872* (2013.01); *G01N 2400/00* (2013.01)
USPC ......................... 424/1.11; 424/1.73

(58) Field of Classification Search
CPC .................... A61K 51/0491; A61K 2201/144; A61K 49/0433
See application file for complete search history.

(56) References Cited

U.S. PATENT DOCUMENTS 5,904,915 A    5/1999  Fujibayashi et al.
6,824,760 B2  11/2004  Tanaka et al.

FOREIGN PATENT DOCUMENTS

EP    2000-595459    * 9/2000  ............. A61K 51/04
JP       59198975 A    * 10/1984

OTHER PUBLICATIONS

Barford et al. (Carb. Res. 1971, 19, 49-61).*
Loike et al. (Am. J. Physiol.-Cell Physiol. 1996, 271, C1774-C1779).*
Fluorine 101 (2013).*
Lopes, D.P. An alternative synthesis of 4-deoxy-4-fluoro-D-glucose and its transport in the human erythrocyte; Carbohydr Res Aug. 1979, vol. 73., abstract.
Petrakova, E. Two methyl tri-O-benzoyl-hex-enopranosides are amongst the products of the reaction of methyl 2,3,6-tri-O-benzoyl-beta-D-galactopyranoside with dimethylaminosulfur trifluoride (DAST); Journal of Carbohydrate Chemistry Apr. 1992, vol. 11. No. 3, abstract.
Maschauer, S. Characterization of 18-F FDG uptake in human endothelial cells in vitro J Nucl Med 2004, vol. 45, pp. 455-460, especially p. 456, p. 457 and figure 2.
Wright, E.M., et al., *Membrane Transport Structure Function and Biogenesis: Residue 457 Controls Sugar Binding and Transport in the Na+/Glucose Cotransporter*, The Journal of Biological Chemistry, vol. 276, No. 52, Issue of Dec. 28, 2001, pp. 49188-49194. (Downloaded from http://www.jbc.org/by guest on Aug. 21, 2013).
Wright, E.M., *Renal N+-glucose cotransporters*, Am J Physiol Renal Physiol, 280:F10-F18, 2001. (Downloaded from pdf.highwire.org on Aug. 21, 2013).

* cited by examiner

*Primary Examiner* — Micheal G Hartley
*Assistant Examiner* — Melissa Perreira
(74) *Attorney, Agent, or Firm* — Christie, Parker & Hale, LLP (57) ABSTRACT

Radiolabeled tracers for sodium/glucose cotransporters (SGLTs), their synthesis, and their use are provided. The tracers are methyl or ethyl pyranosides having an equatorial hydroxyl group at carbon-2 and a C 1 preferred conformation, radiolabeled with $^{18}$F, $^{123}$I, or $^{124}$I, or free hexoses radiolabeled with $^{18}$F, $^{123}$I, or $^{124}$. Also provided are in vivo and in vitro techniques for using these and other tracers as analytical and diagnostic tools to study glucose transport, in health and disease, and to evaluate therapeutic interventions.

27 Claims, 6 Drawing Sheets

CHEMICAL PURITY:
Detection: 10% sulfuric acid in ethanol $R_f$ value: 0.73 for the sample of methyl 4-FDG

FIG. 1

RADIOCHEMICAL PURITY:
Detection: Berthold LB 2832 Linear TLC analyzer $R_f$ value: 0.73 for methyl 4-[F-18]FDG

TRACERS FOR MONITORING THE ACTIVITY OF SODIUM/GLUCOSE COTRANSPORTERS IN HEALTH AND DISEASE

CROSS-REFERENCE TO RELATED APPLICATION

This application is a National Stage patent application under 35 U.S.C. §371 and claims the priority of International Application Number PCT/US2006/020137, filed May 23, 2006, which is based on and claims priority of U.S. Provisional Application No. 60/683,642, filed May 23, 2005.

ACKNOWLEDGEMENT OF GOVERNMENT SUPPORT

This application was made with government support under Grant No. DK19567 (E. Wright), awarded by the National Institutes of Health, UCLA discretionary funds (E. Wright), and DE-FC03-02ER63-420, awarded by the Department of Energy (J. Barrio). The Government has certain rights in the invention.

FIELD OF THE INVENTION

The present invention relates generally to tracers and methods for monitoring glucose metabolism, and more particularly to radiolabeled tracers and methods for monitoring sodium/glucose cotransporters, in vitro and in vivo.

BACKGROUND OF THE INVENTION

Great strides have been made over the past 25 years in the functional imaging of the human body using positron emitters (e.g., carbon-11, fluorine-18, and iodine-124) and positron emission tomography (PET), and gamma-emitting isotopes (e.g. iodine-123) and single-photon emission computed tomography (SPECT). Arguably, the probe that has received the most attention is 2-deoxy-2-[$^{18}$F]fluoro-D-glucose (2-FDG) and, indeed, this sustains the field of clinical PET. 2-FDG is the most widely used PET tracer in the world for in vivo assessment of regional glucose metabolic rates in humans. Approved diagnostic uses with PET include its use for determination of myocardial viability and detection of cancer, epilepsy, and Alzheimer's disease.

The success of 2-FDG PET imaging rests upon the finding that [$^{14}$C]-2-deoxy-D-glucose can be used as a tracer to measure glucose metabolism in brain and other tissues. The human brain consumes about 125 grams of glucose per day and the body goes to extreme measures to deliver this amount across the blood brain barrier. Failure to supply the brain with glucose, for example in hypoglycemia, results in loss of consciousness and even death. Children with genetic defects in glucose transport across the blood brain have severe developmental problems (IQ, motor co-ordination, infantile seizures, etc).

Members of the GLUT family of genes are responsible for glucose uptake into brain across the blood brain barrier (GLUT1) and into neurons and glia (e.g. GLUT3). 2-FDG enters cells and crosses the blood-brain-barrier using facilitated glucose transporters (GLUTs). The glucose analog is phosphorylated by hexokinase to produce 2-deoxy-D-glucose-6-phosphate. Phosphorylated sugars are not substrates for the GLUTs, and 2-deoxy-D-glucose-6-phosphate is not further metabolized. Consequently, 2-deoxy-D-glucose-6-phosphate becomes trapped in cells. Similarly, the radiofluorinated 2-FDG is a substrate for GLUT transporters, is phosphorylated in cells to the 6-phosphate derivative, and becomes trapped.

The accumulation of 2-deoxy-2-[$^{18}$F]fluoro-D-glucose-6 phosphate (2-FDG-6P) in cells permits, using Michaelis-Menten kinetics, determination of the local rates of glucose metabolism in all tissues. PET is employed to image 2-FDG-6P accumulation in living human subjects and animals. 2-FDG PET was first used to much advantage as an experimental tool to monitor regional brain activity in fully conscious subjects, and this revolutionized brain physiology. It was also found that 2-FDG-6P was accumulated in ischemic myocardium, and FDG PET has become a tool to study cardiac pathophysiology.

For at least fifteen years, 2-FDG PET has been used to detect tumors in the body (see, e.g., Czernin Acta Medica Austriaca 69: 162-170, 2002). This is based on the finding that most tumors have a high demand for energy in the form of glucose.

A second pathway for glucose entry into cells exists, the sodium/glucose cotransporter (SGLT) pathway (Wright & Turk (2004); Pflugers Arch. 447:510-518, 2004). However, 2-FDG is a very poor substrate for these glucose transporters, and so 2-FDG PET does not measure glucose utilization into cells by the SGLTs. A hydroxyl group in the equatorial plane of the pyranose ring at carbon-2 is required for binding and transport by SGLTs (Wright (2001) Am. J. Physiol: Renal Physiol. 280: F10-F18; Diez-Sampedro, et al. (2001) J. Biol. Chem. 276:52: 49188-49194). This means that mannose and 2-deoxy-D-glucose are poor substrates for SGLT1 and SGLT2. Mannose, however, is transported by SGLT4 (Tazawa, S. et al. Life Sciences 76: 1039-1050 (2005)).

Similarly, methyl-4-deoxy-D-glucopyranoside and methyl 4-fluoro-4-D-glucopyranoside ("Methyl-4-FDG" or "Me-4-FDG") are not substrates for GLUTs (Wright et al (1980) Biochim. Biophys. Acta. 597:112 124 and unpublished observations), but are excellent substrates for SGLTs, including SGLT1, SGLT2, and SGLT4. The use of Me-4-FDG as an imaging probe for SGLT glucose transporters using PET or analogous imaging techniques (e.g., SPECT) has never been described.

There are two major members of the family of genes coding for SGLTs: SGLT1, which is thought to be expressed mainly in the small intestine, and SGLT2, which is thought to be expressed mainly in the kidney. SGLT1 is primarily responsible for the intestinal absorption of glucose and galactose in the human diet (180-200 grams per day), and mutations in the SGLT1 gene produce the disease Glucose-Galactose Malabsorption (Wright et al (2002) Cell Biochemistry and Biophysics 36; 115-121). SGLT2 is mainly responsible for the reabsorption of glucose from the glomerular filtrate in the kidney (180 grams/day), and mutations in this gene produce the condition known as renal glucosuria (Santer R, et al. J. Am. Soc Nephrol 14:2873-2882, 2003). SGLT4 is also expressed in the intestine and kidney where it appears to be involved in the absorption of D-mannose and fructose (Tazawa, S. et al. Life Sciences 76: 1039-1050, 2005).

It has been commonly believed that SGLT1, SGLT2, and SGLT4 were restricted mainly to the small intestine and kidney. However, it was recently discovered that these genes are expressed throughout the body, including in the heart, lung, brain, prostate, testes, and uterus (Wright & Turk (2004) Pflugers Arch. 447:510-518, Wright unpublished material; Zhou et al (2003) J. Cellular Biochemistry 90:339-346; Tazawa, S. et al. Life Sciences 76: 1039-1050, 2005), and even in metastatic lesions of some tumors (Ishikawa et al (2001) Jpn J. Cancer Res 92: 874-879). We have also found that glucose transporters belonging to the SGLT (SLC5) gene family are also expressed in the brain. SGLT2, SGLT4, and SGLT6 mRNAs are found at high levels in the human whole brain and cerebellum (Wright & Turk, 2004, Wright, unpublished observations) and immunocytochemical studies demonstrate that SGLT1 protein is expressed in specific regions of the hypothalamus, hippocampus, cerebellum and brain stem of rodent and human brains (Poppe, R., et al. (1997) J. Neurochemistry 69:84-94; Hirayama & Wright, unpublished observations).

Therefore, it is reasonable to postulate that the SGLTs play an important role in glucose metabolism in many organs in the body in health and disease. The SGLTs differ from the GLUTs in that they use the sodium gradient across the cell membrane to "pump" sugars into cells to a high concentration (e.g., against a concentration gradient). SGLT1 pumps a non-metabolized substrate (alpha-methyl-D-glucopyranoside) into cells to reach concentrations as high as 800-fold above plasma concentrations (Kimmich (1981) In: Physiology of the Gastrointestinal Tract, Edited by L. R. Johnson et al. Raven Press, New York, pages 1035-1061).

A [$^{11}$C]-methyl-D-glucoside has been synthesized and biologically evaluated as a tracer of sodium dependent glucose transporters. (Bormans et al. J. Nucl. Med 44:1075-1081 (2003)). A commentary on this paper was published in the same issue of the journal. (Gatley. J. Nucl. Med. 44: 1082-1086 (2003)). In addition, three $^{18}$F-fluoro-n-alkyl glucosides have been synthesized and evaluated as potential substrates for sodium/glucose cotransporters. (De Groot et al. J Nucl Med. 44: 1973-81 (2003)). There are limitations with these probes in that the lifetime of [$^{11}$C] is shorter than that of [$^{18}$F] (20.4 vs. 109.8 minutes), and the affinity of the $^{11}$C- and $^{18}$F-fluoro-n-alkyl glucosides for SGLT1 is much lower than that for Methyl-4-[$^{18}$F]-4-deoxy-D-glucose (0.8 to 2.6 mM vs. 50 uM).

Despite the advances made to date, a continuing need exists for efficient molecular imaging probes and methods for probing SGLTs and glucose metabolism in vitro and in living subjects, in healthy and diseased states. Particularly advantageous would be tracers and methods that enable researchers to assess the effect physiological role of the Na/sugar transporters in living human subjects, to monitor different therapeutic interventions on sodium-dependent glucose transport, in vitro and in vivo, and to probe and even distinguish between individual SGLTs (SGLT1, SGLT2, SGLT4, SGLT5, etc.). In addition, a need exists for SGLT probes that cross the blood-brain barrier and thereby enable SGLT activity in the brain to be monitored in vivo.

SUMMARY OF THE INVENTION

According to a first aspect of the invention, it has now been discovered that certain compounds, namely, radiolabeled alkyl pyranosides and free hexoses having an equatorial hydroxyl group at carbon-2, are remarkably well-suited for use as molecular imaging probes (sometimes referred to as "radiographic tracers," "radiolabeled tracers," or simply, "tracers") for sodium/glucose cotransporters, both in vitro and in vivo. In one embodiment of the invention, a tracer for a sodium/glucose cotransporter (SGLT) is provided and comprises a C 1-O-methyl or ethyl pyranoside having an equatorial hydroxyl group at carbon-2, radiolabeled with $^{18}$F, $^{123}$I, or $^{124}$I as more fully described below. In another embodiment, a tracer for a sodium/glucose cotransporter (SGLT) comprises a free hexose having an equatorial hydroxyl group at carbon-2, radiolabeled with $^{18}$F, $^{123}$I, or $^{124}$I. Such free hexoses are capable of crossing the blood-brain barrier, making them ideal for monitoring SGLT activity in the brain.

In one embodiment of the invention, the tracer is provided as a pure alpha or beta anomer. In other embodiments, the tracer is provided as an anomeric mixture (alpha and beta), or even as a mixture of different tracers (e.g., two or more radiolabeled methyl or ethyl pyranosides, two or more radiolabeled free hexoses, one or more radiolabeled methyl or ethyl pyranosides and one or more radiolabeled free hexoses, etc.). A specific example of a tracer according to the invention is the radiofluorinated compound, methyl-4-deoxy-4-[$^{18}$F] fluoro-D-glucopyranoside ("Me-4-[$^{18}$F]-FDG"). It is a specific, high-affinity substrate for SGLTs. Another example of a tracer according to the invention is 1-[$^{18}$F]fluoro-1-deoxy-D-glucose ("1-FDG"). A method of making radiolabeled pyranosides is also provided.

In a second aspect of the invention, a method of detecting the activity of a sodium/glucose cotransporter in vitro is provided, and comprises the steps of obtaining a cellular sample; administering to the cellular sample a radiolabeled tracer of the type described herein; isolating a first aliquot of the cellular sample after a predetermined time interval; assaying the first aliquot for radioactivity; and, after each of one or more additional time intervals, isolating a further aliquot of the cellular sample, and assaying it for radioactivity. Preferably, each aliquot is washed with a buffer solution prior to being assayed for radioactivity. Radiographic techniques include, without limitation, autoradiography, scintillation counting, PET (including micro-PET) and SPECT. This method can be enhanced by using it to monitor the effect on the cellular sample of one or more administered pharmacological or other agents.

In a third aspect of the invention, a method of assessing sodium/glucose cotransporter distribution or activity in a human or non-human mammal, in vivo, is provided, and comprises administering to the mammal a bolus of a tracer as described herein; generating dynamic imaging indicative of tracer uptake in the mammal by scanning the mammal using a radiographic technique; and using the generated radiographic data to assess SGLT distribution or activity in the mammal. One or more regions of interest, e.g., the brain, heart, liver, etc.—or even the mammal's entire body—can be scanned and SGLT activity therein can be monitored dynamically.

In a variation of this method, a tracer that is known to be a substrate for a first SGLT (e.g., SGLT1), but not a second SGLT (e.g., SGLT2 or SGLT4) (or vice versa), is utilized, allowing one to map or probe different metabolic pathways, as well as the effect of external agents on such pathways. By also administering a pharmacological or other agent to the mammal, and monitoring its effect on SGLT activity, one can better assess the agent's usefulness (and/or its deleterious effect) on the mammal.

BRIEF DESCRIPTION OF THE DRAWINGS

These and other features and advantages of the invention will become better understood when considered in conjunction with the following detailed description, and by making reference to the appended drawings, wherein.

DETAILED DESCRIPTION

In accordance with the present invention, novel radiolabeled tracers for sodium/glucose cotransporters (SGLTs), their synthesis, and their use in vivo and in vitro, are provided. According to a first aspect of the invention, a tracer for a sodium/glucose cotransporter (SGLT) comprises (a) a radiolabeled, methyl or ethyl pyranoside having an equatorial hydroxyl group at carbon-2 and a C1 preferred conformation or (b) a radiolabeled free hexose having an equatorial hydroxyl group at carbon-2. Preferably, the pyranoside or hexose is radiolabeled with $^{18}$F, $^{123}$I, or $^{124}$I. In a variant of this aspect of the invention, the tracer is a radiolabeled free hexose having an axial hydroxyl group at carbon-2, i.e., a D-mannose derivative for study of hSGLT4 activity.

As used herein, the term "C1 preferred conformation" means that the more stable conformation of the corresponding pyranose is C1, rather than 1 C, as set forth in Stanek, Jaroslav, et al., The Monosaccharides, Academic Press, New York, 1963, page 67, Table IX). The term "radiolabeled" means that the tracer is isotopically enriched with at least one radioisotope. Table 1 provides a nonlimiting list of radiolabeled tracers according to the present invention.

TABLE 1

Selected Radiolabeled Tracers for SGLTs

A

C 1-O-methyl and ethyl 3-deoxy-3-[$^{18}$F]fluoro-D-glucopyranosides,
C 1-O-methyl and ethyl 4-deoxy-4-[$^{18}$F]fluoro-D-glucopyranosides,
C 1-O-methyl and ethyl 6-deoxy-6-[$^{18}$F]fluoro-D-glucopyranosides,

B

C 1-O-methyl and ethyl 3-deoxy-3-[$^{18}$F]fluoro-D-galactopyranosides,
C 1-O-methyl and ethyl 4-deoxy-4-[$^{18}$F]fluoro-D-galactopyranosides,
C 1-O-methyl and ethyl 6-deoxy-6-[$^{18}$F]fluoro-D-galactopyranosides,

C

C 1-O-methyl and ethyl-3-deoxy-3-[$^{18}$F]fluoro-D-mannopyranosides,
C 1-O-methyl and ethyl-4-deoxy-4-[$^{18}$F]fluoro-D-mannopyranosides,
C 1-O-methyl and ethyl-6-deoxy-6-[$^{18}$F]fluoro-D-mannopyranosides,

D

C 1-O-methyl and ethyl 3-deoxy-3-[$^{123}$I]iodo-D-glucopyranosides,
C 1-O-methyl and ethyl 4-deoxy-4-[$^{123}$I]iodo-D-glucopyranosides,
C 1-O-methyl and ethyl 6-deoxy-6-[$^{123}$I]iodo-D-glucopyranosides,

E

C 1-O-methyl and ethyl 3-deoxy-3-[$^{123}$I]iodo-D-galactopyranosides,
C 1-O-methyl and ethyl 4-deoxy-4-[$^{123}$I]iodo-D-galactopyranosides,
C 1-O-methyl and ethyl 6-deoxy-6-[$^{123}$I]iodo-D-galactopyranosides,

F

C 1-O-methyl and ethyl 3-deoxy-3-[$^{123}$I]iodo-D-mannopyranosides,
C 1-O-methyl and ethyl 4-deoxy-4-[$^{123}$I]iodo-D-mannopyranosides,
C 1-O-methyl and ethyl 6-deoxy-6-[$^{123}$I]iodo-D-mannopyranosides,

G

C 1-O-methyl and ethyl 3-deoxy-3-[$^{124}$I]iodo-D-glucopyranosides,
C 1-O-methyl and ethyl 4-deoxy-4-[$^{124}$I]iodo-D-glucopyranosides,
C 1-O-methyl and ethyl 6-deoxy-6-[$^{124}$I]iodo-D-glucopyranosides, TABLE 1-continued Selected Radiolabeled Tracers for SGLTs

H

C 1-O-methyl and ethyl 3-deoxy-3-[$^{124}$I]iodo-D-galactopyranosides,
C 1-O-methyl and ethyl 4-deoxy-4-[$^{124}$I]iodo-D-galactopyranosides,
C 1-O-methyl and ethyl 6-deoxy-6-[$^{124}$I]iodo-D-galactopyranosides,

I

C 1-O-methyl and ethyl 3-deoxy-3-[$^{124}$I]iodo-D-mannopyranosides,
C 1-O-methyl and ethyl 4-deoxy-4-[$^{124}$I]iodo-D-mannopyranosides,
C 1-O-methyl and ethyl 6-deoxy-6-[$^{124}$I]iodo-D-mannopyranosides,

J

C 1-O-[$^{123}$I]iodomethyl-D-glucopyranosides,
C 1-O-[$^{124}$I]iodomethyl-D-glucopyranosides,

K

C 1-O-[$^{123}$I]iodomethyl-D-galactopyranosides,
C 1-O-[$^{124}$I]iodomethyl-D-galactopyranosides,

L

C 1-O-[$^{123}$I]iodomethyl-D-mannopyranosides,
C 1-O-[$^{124}$I]iodomethyl-D-mannopyranosides,

M

C 1-O-1-[$^{123}$I]iodoethyl-D-galactopyranosides,
C 1-O-2-[$^{123}$I]iodoethyl-D-galactopyranosides,

N

C 1-O-1-[$^{124}$I]iodoethyl-D-galactopyranosides,
C 1-O-2-[$^{124}$I]iodoethyl-D-galactopyranosides,

O

C 1-O-1-[$^{123}$I]iodoethyl-D-mannopyranosides,
C 1-O-2-[$^{123}$I]iodoethyl-D-mannopyranosides,

P

C 1-O-1-[$^{124}$I]iodoethyl-D-mannopyranosides,
C 1-O-2-[$^{124}$I]iodoethyl-D-mannopyranosides,

Q

1-[$^{18}$F]fluoro-1-deoxy-D-glucose
3-[$^{18}$F]fluoro-3-deoxy-D-glucose

R

1-[$^{18}$F]fluoro-1-deoxy-D-galactose
3-[$^{18}$F]fluoro-3-deoxy-D-galactose
4-[$^{18}$F]fluoro-4-deoxy-D-galactose
6-[$^{18}$F]fluoro-6-deoxy-D-galactose

S

1-[$^{123}$I]iodo-1-deoxy-D-glucose
3-[$^{123}$I]iodo-3-deoxy-D-glucose
4-[$^{123}$I]iodo-4-deoxy-D-glucose
6-[$^{123}$I]iodo-6-deoxy-D-glucose

T

1-[$^{123}$I]iodo-1-deoxy-D-galactose
3-[$^{123}$I]iodo-3-deoxy-D-galactose
4-[$^{123}$I]iodo-4-deoxy-D-galactose
6-[$^{123}$I]iodo-6-deoxy-D-galactose

U

1-[$^{124}$I]iodo-1-deoxy-D-glucose
3-[$^{124}$I]iodo-3-deoxy-D-glucose
4-[$^{124}$I]iodo-4-deoxy-D-glucose
6-[$^{124}$I]iodo-6-deoxy-D-glucose

V

1-[$^{124}$I]iodo-1-deoxy-D-galactose
3-[$^{124}$I]iodo-3-deoxy-D-galactose
4-[$^{124}$I]iodo-4-deoxy-D-galactose
6-[$^{124}$I]iodo-6-deoxy-D-galactose

W

1-[$^{18}$F]fluoro-1-deoxy-D-mannose
3-[$^{18}$F]fluoro-3-deoxy-D-mannose
4-[$^{18}$F]fluoro-4-deoxy-D-mannose
6-[$^{18}$F]fluoro-6-deoxy-D-mannose TABLE 1-continued Selected Radiolabeled Tracers for SGLTs

X

1-[$^{123}$I]iodo-1-deoxy-D-mannose
3-[$^{123}$I]iodo-3-deoxy-D-mannose
4-[$^{123}$I]iodo-4-deoxy-D-mannose
6-[$^{123}$I]iodo-6-deoxy-D-mannose

Y

1-[$^{124}$I]iodo-1-deoxy-D-mannose
3-[$^{124}$I]iodo-3-deoxy-D-mannose
4-[$^{124}$I]iodo-4-deoxy-D-mannose
6-[$^{124}$I]iodo-6-deoxy-D-mannose

Z $^{11}$C-labeled analogs of C 1-O-methyl pyranosides bearing a $^{11}$C methyl group at carbon-1, 3, 4, or 6, and having an equatorial hydroxyl group at carbon-2

AA $^{11}$C-labeled analogs of C 1-O-methyl-halo-deoxy-pyranosides bearing a $^{11}$C methyl group at carbon-1, 3, 4, or 6, and having an equatorial hydroxyl group at carbon-2, e.g., [$^{11}$C]-methyl-4-deoxy-4-fluoro-D-glucose, [$^{11}$C]-methyl-4-deoxy-4-fluoro-D-mannose, etc.

In one embodiment, the tracer is provided as a substantially pure alpha or beta anomer of a single compound of the type listed above in Table 1. Alternatively, the tracer is provided as a racemic mixture of anomers of a single compound. In still another embodiment, the tracer is provided as a mixture of two or more different pyranosides, free hexoses, or mixtures thereof, with each tracer being anomerically pure or a mixture of alpha and beta anomers.

A nonlimiting example of a radiolabeled tracer according to the present invention is methyl 4-deoxy-4-[$^{18}$F]fluoro-D-glucopyranoside ("Me-4-[$^{18}$F]-FDG"), synthesized in either of its two anomeric forms, alpha-methyl 4-[$^{18}$F]-FDG and beta-methyl 4-[$^{18}$F]-FDG, or as a racemic mixture. Micro-PET tests in rodents, and PET tests in non-human primates (Vervet monkeys) and human volunteers, confirm that Me-4-[$^{18}$F]-FDG, in both of its two anomeric forms, is a substrate for sodium-dependent glucose transporters (SGLTs), but not a substrate for GLUTs. For example, Me-4-[$^{18}$F]-FDG is not a substrate for GLUT1 in the blood brain barrier. It is a novel, high affinity tracer for SGLTs in those cells expressing SGLTs.

Advantageously, Me-4-[$^{18}$F]-FDG is accumulated to high concentrations and will not enter or leave cells by the transporters (GLUTs) that handle 2-FDG. It can be used as a tracer for SGLT activity in both in vivo and in vitro studies. This is exemplified by methyl 4-fluoro-4-deoxy-D-glucopyranoside, which has a $K_m$ for SGLT1 of 50 µM, an order of magnitude lower than for D-glucose transport by SGLT1.

Another example of a radiolabeled tracer according to the invention is 1-[$^{18}$F]fluoro-1-deoxy-D-glucose ("1-FDG").

Synthesizing the radiolabeled tracers listed in Table 1 is straightforward. For example, starting from readily available sugars or their methyl or ethyl glycopyranosides having a C1 or 1 C conformation and an equatorial hydroxyl group at carbon-2 (e.g., glucopyranosides, galactopyranosides, allopyranosides, gulopyranosides), the sequence entails (a) protection of the hydroxyl group at the desired ring location (e.g., carbon-1, 3, 4, or 6) with an appropriate protective group; (b) acetylation (to protect all other hydroxyl groups); (c) removal of the specific protection from the hydroxyl group at the desired ring location (e.g., carbon-1, 3, 4, or 6); (d) triflate or tosylate formation by reaction of the hydroxyl group at the desired ring location (e.g., carbon-1, 3, 4, or 6) with a reactive derivative of trifluoromethyl or phenyl sulfonic acid; (e) nucleophilic displacement by a radiohalide ion ($^{18}$F$^-$, $^{123}$I$^-$, or $^{124}$I$^-$), which occurs with inversion of configuration at the desired ring location (e.g., carbon-1, 3, 4, or 6); and (f) deacetylation (hydrolysis). The radiohalide ions are obtainable by either cyclotron production at the site in the case of short-lived [$^{18}$F]fluorine (half life: ~110 min), or from commercial sources ($^{123}$I$^-$, or $^{124}$I$^-$). Alternatively, a tracer is formed by halogen-to-fluoride exchange with [$^{18}$F]fluoride from the halo-substituted pyranoside of interest.

The α or β anomers, or a racemic mixture of α and β anomers, can be prepared by selecting the desired starting isomer and/or by using standard isomeric separation techniques.

The general methodology for preparing radiolabeled tracers according to the invention, starting with methyl 2,3,6-tri-O-acetyl-4-trifyl-D-galactopyranoside, is presented below in Example 1. The resulting radiolabeled compound is methyl 4-deoxy-4-[$^{18}$F]fluoro-β-D-glucopyranoside:

where "OTfl" is triflate; "OAc" is acetyl, and "OMe" is methoxy.

Additional information on the synthesis of halogenated hexoses is found in Dax K., et al. 2000, Carbohydrate Res 327: 47-86). The synthesis of 4-[$^{18}$F]fluoro-4-deoxy-D-glucose is reported in Longford, C. P. D., Goodman, M. M., Kabalka, G. W., Besozzi, M. C., Hubner, K. F., Smith, G. T.: Fluorine-18 4-fluoro-4-deoxy-D-glucose: a potential brain, heart, and tumor imaging agent. J. Nucl. Med. 1992, 33, 983. The synthesis of 6-[$^{18}$F]fluoro-6-deoxy-D-glucose is reported in Neal et al, J Label Compd Radiopharm 2005: 48:845-854. The synthesis of 6-Fluoro-6-deoxy-D-galactose is described in Christman et al, J Label Compd Radiopharm 1977, 13:283; 1977b J Label Compd Radiopharm 13:555-559), Ishiwata et al. 1989, Nucl Med Biol 16:775-781. The synthesis of 6-[$^{123}$I]iodo-6-deoxy-D-glucose is described in Henry C. et al. 1997; Nucl Med & Biol 24:527-534. Iodination of glucose with [$^{123}$I] at carbon numbers 1, 2, or 3 is described in Koumanov F. et al. 1996, Nucl Med & Biol. 23: 53-60.

In a second aspect of the invention, a method of detecting a sodium/glucose cotransporter in vitro is provided, and comprises the steps of obtaining a cellular sample, administering to the cellular sample a radiolabeled tracer; isolating a first aliquot of the cellular sample after a predetermined time interval; assaying the first aliquot for radioactivity; and, after each of one or more additional predetermined time intervals, isolating a further aliquot of the cellular sample and assaying it for radioactivity. Preferably, the first and subsequent aliquots are washed with a buffering solution prior to being assayed for radioactivity.

Radiographic techniques include, without limitation, autoradiography, scintillation counting, PET (including micro-PET), and SPECT. In a variation of the method, one or more pharmacological or other agents are administered to the cellular sample, and the effect of the agent(s) is monitored.

In one embodiment of the invention, the tracer is one or more of the compounds listed in Table 1. In another embodiment, the tracer is [$^{14}$C]-labeled or [$^{3}$H]-labeled methyl 4-FDG—which can be obtained from commercial sources, e.g., Moravek Biochemistry, Inc. (Brea, Calif.). In still another embodiment, either or both of the known compounds 4-[$^{18}$F]fluoro-4-deoxy-D-glucose ("4-[$^{18}$F]FDG") or 6-[$^{18}$F] fluoro-6-deoxy-D-glucose ("6-[$^{18}$F]FDG") is used as a tracer. Literature references to both compounds are provided above. In another embodiment of the invention, [$^{11}$C]-radiolabeled methyl pyranosides, analogous to those listed in Table 1 are used a tracers for SGLTs. Example 2, below, describes the synthesis of O—[$^{11}$C]-methyl 4-FDG. The other methyl pyranosides are prepared in an analogous manner, using $^{11}$C-methylation of the appropriate protected 1-hydroxy precursor. Although $^{11}$C has a half-life of only 20 minutes, a tracer containing the radioisotope could be prepared just prior to administration, and its uptake in the subject's body monitored. Combinations of different tracers, of the type described herein or elsewhere in the literature, also can be utilized in the practice of the invention.

Nonlimiting examples of cellular samples include a single mammalian cell, a plurality of mammalian cells, a tissue sample, and mixtures thereof. Where a plurality of cells is employed, it may consist of a genetically related cell line or a collection of unrelated cells of the same or different species.

Nonlimiting examples of pharmacological agents include sodium ion, phlorizin, glucose, and galactose. Mixtures of agents may be employed.

The following references describe methods for assaying radioactive uptake in isolated tissues and cells: (1) Kippen, I., Klinenberg, J. R., and Wright, E. M. (1980), Effects of metabolic intermediates on sugar and amino acid uptake in rabbit renal tubules and brush border membranes. J. Physiol. 304: 373 387; (2) Ikeda, T. S., Hwang, E-S., Coady, M. J., Hirayama, B. A., Hediger, M. A. and Wright, E. M. (1989), Characterization of a Na+/glucose cotransporter cloned from rabbit small intestine. J. Membrane Biol. 110:87-95; (3) Korn T, Kuhlkamp T, Track C, Schatz I, Baumgarten K, Gorboulev V, Koepsell H., The plasma membrane-associated protein RS1 decreases transcription of the transporter SGLT1 in confluent LLC-PK1 cells. J Biol Chem. Nov. 30, 2001; 276(48): 45330-40.

In a third aspect of the invention, in vivo methods of monitoring SGLTs in mammals, in health and disease, are provided. In one embodiment, a bolus of a radiolabeled tracer is administered to a mammal; radiographic data indicative of tracer uptake is generated by scanning the mammal using a radiographic technique, (e.g., autoradiography, scintillation counting, PET (including micro-PET), SPECT, etc.); and the generated radiographic data is used to probe or assess SGLT distribution or activity in the mammal. The tracer can be a compound listed in Table 1, [$^{14}$C]-labeled or [$^{3}$H]-labeled methyl 4-FDG, 4-[$^{18}$F]FDG, 6-[$^{18}$F]FDG, O-[$^{11}$C]-methyl 4-FDG or analogous [$^{11}$C]-radiolabeled methyl pyranoside, or another compound that functions as a substrate for SGLTs. The invention can be used to monitor SGLT distribution and function in mammals, including humans (normal and those with defective SGLT genes), non-human primates, and rodents. The use of wild type, transgenic, and/or knockout rodents can be particularly useful.

A particularly beneficial use of the invention is the administration of one or more SGLT tracers capable of penetrating the blood-brain barrier to monitor SGLT distribution in the healthy, diseased, or injured brain of a human or other mammal. In one embodiment, a bolus of 4-[$^{18}$F]FDG is administered to a human or other mammal, and radiographic data indicative of tracer uptake in the subject's brain is generated by scanning the brain using a radiographic technique, (e.g., autoradiography, scintillation counting, PET (including microPET), SPECT, etc.). The generated radiographic data can be used to probe or assess SGLT distribution or activity in the subject's brain. In other embodiments, other radiolabeled free hexoses (as recited, e.g., in Table 1), which are capable of crossing the blood-brain barrier, are utilized as the tracer, alone or in combination.

It will be appreciated that a number of variations are included within this aspect of the invention. For example, in one embodiment, the therapeutic effect of a pharmacological or other agent on a sodium/glucose cotransporter in a mammal is evaluated by (i) administering to a mammal a single bolus or multiple boluses of a radiolabeled tracer, e.g., a tracer recited in Table 1; (ii) generating a first set of radiographic data by scanning the mammal using a radiographic technique; (iii) administering to the mammal a single bolus or multiple boluses of an actual or putative therapeutic agent; (iv) generating a second set of radiographic data by scanning the mammal using a radiographic technique; and (v) comparing the first and second sets of radiographic data. In another embodiment, the method comprises (i) administering to a mammal a bolus of an actually or putatively therapeutic agent; (ii) administering to the mammal a bolus of a radiolabeled tracer, e.g., a tracer as recited in Table 1; (iii) generating a set of radiographic data by scanning the mammal using a radiographic technique; and (iv) comparing the radiographic data to data obtained in the absence of the agent—i.e., data previously (or subsequently) obtained from the same mammal or from a different mammal. One or more tracers in addition to those listed in Table 1 can be substituted for or used in combination with the tracers described herein.

In another variation of this aspect of the invention, the method of monitoring sodium/glucose cotransporter activity in a mammal, in vivo, comprises administering to a mammal a bolus of a tracer known to be a substrate for a first specified sodium/glucose cotransporter (, e.g., SGLT1, SGLT2, SGLT4, etc.), but not a substrate for a second specified sodium/glucose cotransporter; generating radiographic data indicative of tracer uptake in the mammal by scanning the mammal using a radiographic technique; and using the radiographic data to assess the specified SGLT's distribution or activity in the mammal. For example, in one embodiment, the tracer is Me-4-[$^{18}$F]-FDGalactose, which is a substrate for SGLT1, but not SGLT2. In another embodiment, the tracer is Me-4-[$^{18}$F]-FDMannose, which is a substrate for SGLT4, but not SGLT1 or 2. Advantageously, the radiographic technique can include, or be used in conjunction with, a computerized tomographic (CT) technique to scan or rescan all or part of the mammal's body, thereby providing an anatomical determination of the test animal and, hence, quantitation of tracer uptake into tissues and organs, both in the presence and in the absence of one or more pharmacological or other agents. Whole body, dynamic body, dynamic brain, and dynamic pelvic/abdominal scans can be carried out. Whole body microPET in rodents can be employed to monitor SGLT activity.

Optionally, additional information can be obtained by also administering one or more pharmacological or other agents to the animal, and monitoring the effect of the agent(s) on tracer uptake and distribution. Nonlimiting examples of suitable agents, include sodium ion, glucose, galactose, and phlorizin. Phlorizin is a non-toxic compound and is a competitive, non-transported blocker of sugar transport by SGLT1 and 2 (SGLT1 Ki<1 μM). Any therapeutic agent can also be used to evaluate its potential role and in vivo activity on SGLTs in various organs, using in vivo competitive kinetics with the radiolabeled tracer.

In one embodiment of the invention, the activity of SGLTs is determined by pharmacological experiments. Nonlimiting examples include: (1) intravenous injection of the specific SGLT blocker phlorizin, and (2) intravenous infusion of known competitive blockers of sugar uptake by SGLT1 (blocked by excess, >500 micromolar, methyl-alpha4-deoxy-4-fluoro-D-glucopyranoside or excess, >10 mM D-galactose) or SGLT2 (blocked by D-glucose, but not by D-galactose).

It has been found that imaging methods and analytic methods currently practiced for GLUTs (using FDG) are readily utilized with the tracers described herein to assess SGLT distribution and activity. The following references describe PET, micro-PET, and autoradiographic techniques that will be useful in practicing the invention: (1) Phelps M. E. PET Molecular imaging and its biological applications Springer, New York (2004), including Chapter 1. Cherry, S. R. & Dahlborn, M. PET Physics, Instrumentation and Scanners; Chapter 2 Gambhir, S. S. Quantitative Assay Development for PET; Chapter 4. Barrio, J. R. The Chapter 7. Silverman D. H. S. & Melega, W. P. Molecular imaging of biological process with PET. (2) Moore T H, et al. Quantitative assessment of longitudinal metabolic changes in after traumatic brain injury in the adult rat using FDG-microPET. J Cereb Blood Flow Metab. 20(10):1492-501, (2000); and (3) Matsumura A, et al. Assessment of microPET performance in analyzing the rat brain under different types of anesthesia: comparison between quantitative data obtained with microPET and ex vivo autoradiography. Neuroimage 20: 2040-2050 (2003).

The kinetics of tracer uptake is obtained by tracer kinetic modeling (see for example Carson R. E. Tracer Kinetic Modeling. In: Valk P. E. et al. Positron Emission Tomography, Springer, 2003, and Gambhir, S. S. Quantitative Assay Development for PET. In: Phelps M. E. PET Molecular imaging and its biological applications Springer, N.Y., 2004; Bertoldo, A. et. al. (2005) J. Clinical Endocrinology & Metabolism, 90:1752-1759.

Quantitative comparisons of uptakes observed with patients and with normal control subjects will provide information about pathologies. For example, in tumors that use SGLTs to obtain glucose as a fuel, these SGLT tracers will be used to stage the tumor and to monitor the effectiveness of surgery, and chemo- and/or radiation therapy. The methodology is similar to that used for the diagnosis; staging, restaging and monitoring of tumors that accumulate 2-FDG (see Czemin, J. Oncological applications of FDG PET. In: PET, Molecular Imaging and its Biological Applications, Ed: Phelps, M. E. Springer, N.Y. 2004). It is noted that some tumors consume glucose more anaerobically than most, and since 2-FDG uptake is very sensitive to these variations, the in vivo method is thus restricted in its utility for diagnostic purposes (i.e., it has reduced sensitivity for detection).

Oral administration of the tracers will provide information about the functional activity of SGLTs in the intestine, i.e. determination of the amount of tracer uptake into the body provides a measure of functional integrity of the intestine in health and disease, and localization of tracer uptake in the mucosa of the intestine provides a direct measure of SGLT1 activity in the brush border membrane (this will be established in studies comparing patients with mutations in SGLT1 to normal subjects). The accumulation, or lack thereof, of tracer in the intestinal mucosa will provide a direct functional index of the intestinal absorptive function in patients with disease such as irritable bowel syndrome (IBS) and inflammatory bowel disease (IBD).

Use of tracers for in vivo and in vitro monitoring of drug effects on SGLTs should allow researchers to evaluate site of action, dose dependency, length of action and other pharmacokinetic and pharmacodynamic parameters of the drug in animals or human subjects. For example, in one embodiment of the invention, a radiolabeled tracer as described herein is administered to a subject, and PET imaging is used to monitor the effects of drugs on the absorption of tracer from the gut, the reabsorption of tracer from the glomerular filtrate and the uptake of tracer into organs, tissues and tumors. The imaging studies can be carried out before, during and after drug administration. As an example such drug studies include those designed to promote glucose excretion by the kidneys, block glucose uptake into tumors, and chemotherapeutics.

Methyl 4-[$^{18}$F]FDG in particular promises to be a useful diagnostic probe for the following:
(1) Disorders of intestinal and renal function: In the case of the small intestine it will be used as a diagnostic tracer for intestinal function in patients with malabsorption syndromes, IBS, IBD, Crohn's disease.
(2) In the kidney it will be a useful probe to evaluate renal failure, renal function in diabetes, and the function of transplanted kidneys.
(3) Uptake of methyl 4-FDG into heart may also be useful for diagnostic purposes in heart failure as SGLT genes are expressed in cardiac myocytes.

Methyl-4-FDG transport into tumors will also be useful in the diagnosis of various forms of cancer. Methyl-4-FDG can be specially useful in the diagnosis of prostate cancer not only because of the presence of SGLTs in this tumor, but also because methyl 4-FDG is essentially not excreted via kidney to the urinary bladder, enhancing visibility of the primary tumor and adjacent lymph nodes, normally obscured with molecular imaging probes (e.g. 2-FDG) with rapid kidney excretion.

The radiolabeled free hexose tracers (types L-Q in Table 1) should prove to be particularly beneficial as probes for SGLT activity and glucose metabolism in the brain, because of the ability of the probes to cross the blood-brain barrier. This will enable medical practitioners to monitor SGLT activity in the brain of patients suffering from Alzheimer's disease, Parkinson's disease, other forms of dementia, brain tumors, brain injury and trauma, stroke, epilepsy, and other conditions, prior to, during, or after the administration of a pharmaceutical or therapeutical agent. Using radiolabeled alkyl pyranosides and free hexoses of the type described herein, it will also be possible to monitor SGLT activity in muscles, diabetics, organ transplants, etc.

The following are nonlimiting examples of the invention.

Example 1

Methyl-4-deoxy-4-[$^{18}$F]fluoro-alpha-D-glucopyranoside

Methyl 2,3,6-tri-O-acetyl-4-O-trifyl-alpha-D-galactopyranoside and methyl 2,3,6-tri-O-acetyl-4-O-trifyl-beta-D-galactopyranoside were prepared following the procedures described in the literature. (Kiefel M J; Beisner B; Bennett S; Holmes I D; von Itzstein M: Synthesis and biological evaluation of N-acetylneuraminic acid-based rotavirus inhibitors. Journal of Medicinal Chemistry 1996, 39, 1314-1320.)

[$^{18}$F]Fluoride was prepared by proton bombardment of [$^{18}$O] enriched water via [$^{18}$O](p,n)[$^{18}$F] nuclear reaction. At the end of the bombardment, activity was transferred into a solution of 1 mg of potassium carbonate and 10 mg of Kryptofix 2.2.2 in 40 μL of water and 960 μL of acetonitrile. The volatile components were evaporated under a stream of nitrogen at 110° C. and the residual moisture was co-evaporated with acetonitrile (3×0.5 mL).

Methyl 2,3,6-tri-O-acetyl-4-O-trifyl-beta-D-galactopyranoside (5 mg) dissolved in 1 mL of dry acetonitrile was subsequently added to the radiofluoride, and the mixture was heated for 15 min at 90° C. The solvent was evaporated under a stream of nitrogen while the bath temperature was being increased to 110° C. The residue was treated with 1 mL of 1N HCl solution at 110° C. for 15 min. The resulting mixture was passed through a cation/anion exchange resin column (0.8× 20 cm), Waters alumina Sep-Pak cartridge (pre-washed with 20 mL of water), Waters C18 Sep-Pak cartridge (pre-washed with 5 mL of methanol and 2×6 mL of water) in the given order. The solution was finally passed through a 0.2 µm sterile filter into a sterile vial containing 1 mL of 9% NaCl solution. An additional 7.5 mL of water was added through the filter in order to bring the final concentration to 0.9% NaCl. The radiochemical yield was 70-82% after 70 min of total synthesis time (n=9).

Radiochemical yields range from 69-92% (n=6) after 65-70 min of overall synthesis time. The radiochemical purity of the product was checked by radio TLC performed on silica gel plates, using a mixture of acetonitrile and water (85/15) as the mobile phase. The retention factor of the only radioactive peak detected was determined to be 0.73 (determined by radioTLC after the starting point and the solvent front were both marked with a small amount of the product). Typical specific activities (activity/mass) are in the range 0.1 to >30 Ci/micromole. The non-radioactive [$^{19}$F]fluorine-labeled products, methyl 4-deoxy-4-fluoro-alpha-D-glucopyranoside and methyl 4-deoxy-4-fluoro-beta-D-glucopyranoside, were prepared for the purpose of identifying the [$^{18}$F]fluorine-labeled analogs, by reacting methyl 2,3,6-tri-O-acetyl-alpha-D-galactopyranoside and methyl 2,3,6-tri-O-acetyl-beta-D-galactopyranoside, respectively, with DAST in dichloromethane followed by de-acetylation with acid. Both compounds are well characterized in the literature. (Card P J; Reddy G S: Fluorinated carbohydrates. Selective fluorination of gluco- and mannopyranosides. Use of 2-D NMR for structural assignment. Journal of Organic Chemistry 1983, 48, 4737-4743; Petralkova E; Yeh H J C; Kovac P; Glaudemans C P J: Two methyl tri-O-benzoylhexenopyranosides are amongst the products of the reaction of methyl 2,3,6-tri-O-benzoyl-beta-D-galactopyranoside with DAST. Journal of Carbohydrate Chemistry 1992, 11, 407-12; respectively)

Methyl 4-deoxy-4-fluoro-alpha-D-glucopyranoside: 1H-NMR δ 3.45 (3H, s, OMe), 3.46 (1H, ddd, H-2), 3.71-3.75 (2H, m, H-5 and H-6), 3.82 (1H, m, H-6'), 3.89 (1H, ddd, H-3), 4.26 (1H, d, H-1), 4.72 (1H, ddd, H-4); 19F-NMR δ 195.1

Methyl 4-deoxy-4-fluoro-beta-D-glucopyranoside: 1H-NMR δ 3.31 (1H, ddd, H-2), 3.61(1H, m, H-5), 3.66 (3H, s, OMe), 3.77 (1H, ddd, H-3), 3.84 (1H, ddd, H-6), 3.97 (1H, dt, H-6'), 4.36 (1H, d, H-1), 4.37 (1H, ddd, H-4); 19F-NMR δ 196.84.

Both chemical and radiochemical purity of methyl 4-deoxy-4-[$^{18}$F]fluoro-alpha-D-glucopyranoside (methyl 4-[$^{18}$F]FDG) and methyl 4-deoxy-4-[$^{18}$F]fluoro-beta-D-glucopyranoside (methyl 4-[$^{18}$F]FDG-) were determined using thin-layer chromatography (TLC) performed on silica (solid phase) TLC plates (Whatman A L SIL G/UV), using a mixture of acetonitrile and water (85% and 15%, respectively) as the mobile phase. The compounds were detected by spraying a TLC plate with 10% sulfuric acid in ethanol and heating it at 100° C.

Figure 1:
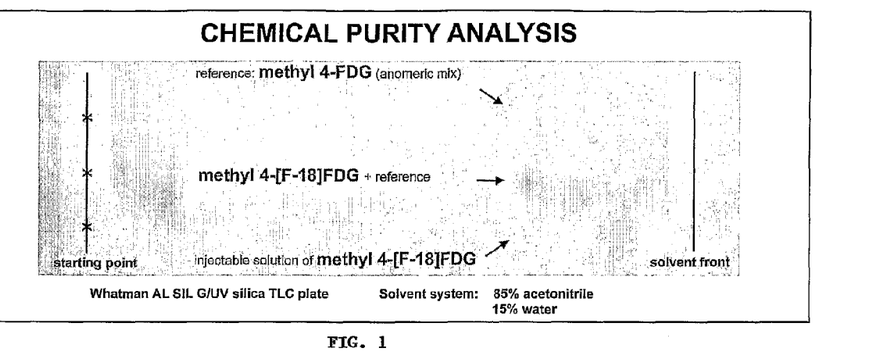
FIG. 1 is depiction of a TLC plate for a chemical purity analysis of Me-4-[$^{18}$F]FDG, prepared in accordance with one embodiment of the present invention.

FIG. 1 depicts a TLC plate showing the results of such analysis of an injectable solution of 4-deoxy-4-[$^{18}$F]fluoro-alpha-D-glucopyranoside (methyl 4-[$^{18}$F]FDG) (lower row). The mass of the compound was very low, below the detection limit of the detection method used, therefore no spot was observed. In addition no presence of other chemical compounds in the solution was noticed.

Figure 2:
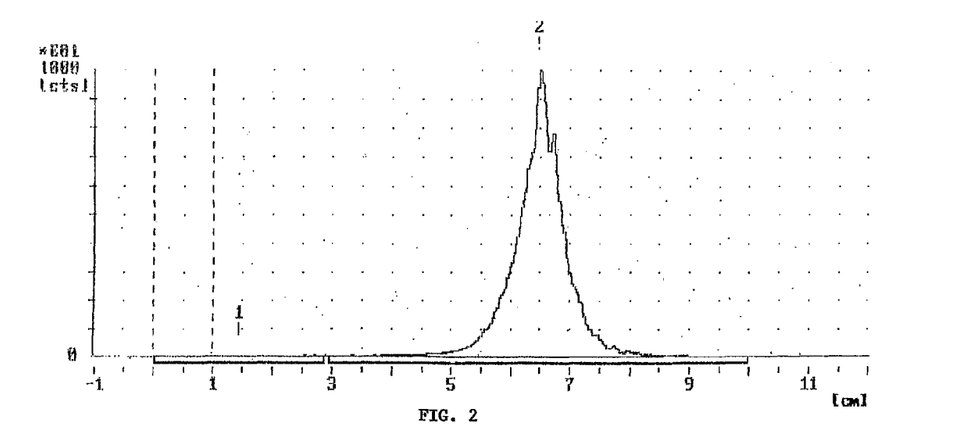
FIG. 2 is a graph of radiochemical purity of Me 4-[$^{18}$F] FDG, prepared by analyzing the TLC plate referred to in FIG. 1 using a linear radiation detector.

As a reference, a sample of methyl 4-FDG (anomeric mix) was also analyzed on the same plate (upper row) alone, and in the mix with methyl 4-[$^{18}$F]FDG (middle row). The observed spot for methyl 4-FDG had the retention factor of 0.73 (upper and middle row). When the same plate was analyzed with a linear radiation detector (Berthold L B 2832 Linear TLC analyzer), only one radioactive peak was detected (FIG. 2). This peak has the retention factor of 0.73 and corresponds to methyl 4-[$^{18}$F]FDG.

Example 2

Radiosynthesis of O-[$^{11}$C]-Methyl-4-FDG

This procedure is a modification of the one described by Bormans et al., J. Nucl. Med 44:1075-1081 (2003) for $^{11}$C-methyl glucose. [$^{11}$C]—CH$_3$I was synthesized from [$^{11}$]CO$_2$ using standard procedures well established in the literature. [$^{11}$C]-methyl triflate was obtained by passage of [$^{11}$C]-CH$_3$I over a Ag-triflate column at 180° C. [$^{11}$C]-methyl triflate was bubbled through a solution of 3 mg of 4-FDG (prepared as described above) in a mixture of 0.5 mL of 0.05 mol/L NaOH and 1 mL of acetone for 5 min at room temperature. The solution was then neutralized with phosphate buffer, pH 6 (0.5 mol/L), and acetone was evaporated by careful heating under a stream of helium. The resulting solution was diluted with saline to an appropriate radioactive concentration for in vivo studies. For biodistribution of the individual alpha and beta-anomers, the anomeric mixture was separated using high-performance liquid chromatography (HPLC) with an Aminex HPX-87c column (Bio-Rad) (300_7.8 mm) eluted with water at a flow rate of 0.5 mL/min. The alpha and beta anomers of [$^{11}$C]-methyl 4-FDG were found to coelute with the anomers of methyl 4-FDG. The purified alpha and beta anomers were diluted with saline to an appropriate radioactive concentration for use in in vivo studies.

Example 3

Use of a Tracer as an In Vitro Marker of SGLTs

Procedures aimed at detecting radioactivity (e.g. autoradiography) are used to map distribution and function (e.g. pharmacological blockade) of SGLTs in individual cells, cell lines, tissue specimens, etc. Isolated tissue specimens, cells, or cell lines are incubated in media under physiological conditions of pH, temperature, and oxygenation. A radiolabeled tracer as described above is added and, at various time intervals, aliquots of the tissue/cells are removed and washed free of the tracer with ice-cold buffers. The radioactivity in the whole tissue or cell sample is assayed using a counter (e.g., a gamma or liquid scintillation counter), and the uptake (moles) at each time point is calculated (corrected for time decay and normalized for the quantity of tissue/cells used). The tracer uptake is optionally measured in the presence and absence of one or more competitive agents for SGLTs, e.g., sodium, phlorizin, glucose, galactose, pharmaceutical agent (e.g., a blocker to lower blood glucose by inhibiting the reabsorption of glucose from the glomerular filtrate (e.g., Tsujihara, K. et al. Chem Pharm. Bull. 44: 1174-1180, 1986)), etc. The sensitivity of uptake to Na and phlorizin are the hallmarks of SGLT transporters, and the differential sensitivity to glucose and galactose permits the distinction between SGLT1 and SGLT2 activity.

Example 4

Use of a Tracer for In Vivo Mapping and Analysis of Function of SGLTs in Non-Human Mammals A bolus of a radiolabeled tracer is administered to a non-human primate, rodent, or other non-human mammal, intravenously or orally, and the distribution of tracer transport activity is followed by radiographic means, e.g., PET, micro-PET and/or SPECT. For PET, an intravenous dose of the tracer contains ~200 µC/Kg (body weight) methyl 4-[$^{18}$F] fluoro-4-deoxy-D-glucopyranoside dissolved in <1 ml saline. Alternatively, an oral dose is introduced directly into the animal's stomach, e.g., in rats 200 µC in a volume of 0.3 to 3 ml in a vehicle of varying composition (isotonic salines with and without Na, sugars, and blockers), by gavage tube. The identity of each organ and tissue taking up the tracer is confirmed by CT scans. Scans can be conducted both with and without administering one or more pharmacological agents, e.g., sodium, phlorizin, glucose, galactose, etc.

Figure 3:
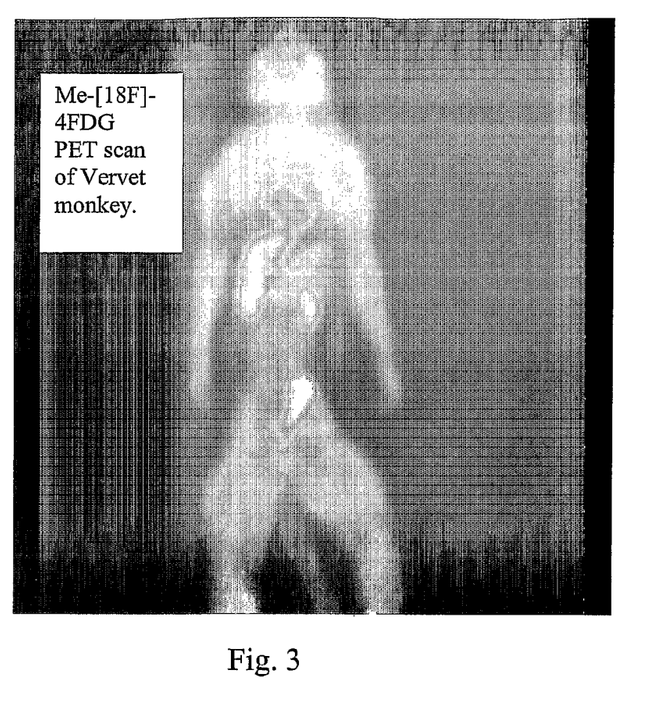
FIG. 3 is a Me-4-[$^{18}$F]-FDG PET scan of a vervet monkey.

FIG. 3 is a nonlimiting example of a methyl 4-[$^{18}$F]-FDG whole body PET scan of a Vervet monkey. The tracer is accumulated in the liver, heart, and kidneys, but not in the brain and little in the urinary bladder.

Figure 7:
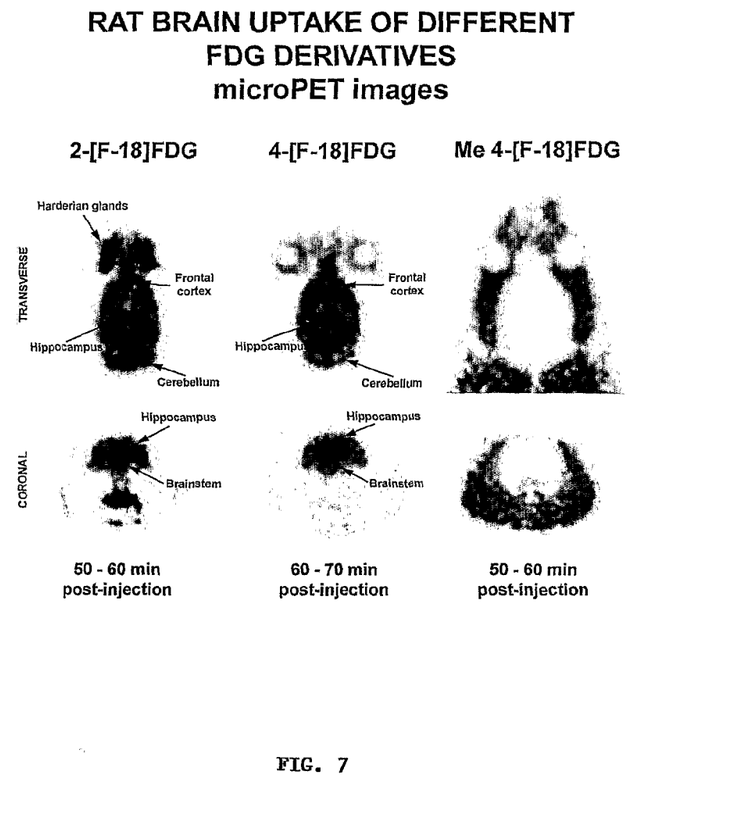
FIG. 7 shows MicroPET images of a rat's brain after injection with 2-[$^{18}$F]-FDG, 4-[$^{18}$F]-FDG, and Me-4-[$^{18}$F]-FDG, respectively.

FIG. 7 presents MicroPET images of a rat's brain after injection of radiofluorinated glucose derivatives. On the left hand side are shown the images acquired between 50 min and 60 min after the intravenous injection of 2-[$^{18}$F]fluoro-2-deoxy-D-glucose (2.41 mCi as bolus). The middle column shows the brain microPET images acquired at 60 min to 70 min after intravenous injection of 2.60 mCi of 4-[$^{18}$F]fluoro-4-deoxy-D-glucose. The right hand column shows the head microPET images acquired at 50 min to 60 min after intravenous injection of 2.81 mCi of methyl 4-[$^{18}$F]fluoro-4-deoxy-D-glucopyranoside. These experiments were performed in the same animal at three different occasions. Note the lack of brain uptake of methyl 4-[$^{18}$F]fluoro-4-deoxy-D-glucopyranoside, which is not transported across the blood-brain barrier. In contrast, both 4-[$^{18}$F]fluoro-4-deoxy-D-glucose and 2-[$^{18}$F]fluoro-2-deoxy-D-glucose cross the blood-brain barrier and accumulate in the brain. The images were acquired using a Concorde 220 microPET camera (Siemens/CTI, Knoxville, Tenn.). The animal was kept under anesthesia with 2% isoflurane in oxygen during all three experiments. Injectable solutions of all radiotracers were prepared in normal saline (0.9% NaCl).

Example 5

Use of a Tracer for In Vivo Mapping and Analysis of Function of SGLTs in Humans

A bolus of a radiolabeled tracer is administered to a human subject, orally or by intravenous injection, and its uptake into the organs and tissues of the body is followed radiographically. For a 50-70 kg person, 10 mC of methyl 4-deoxy-4-[$^{18}$F]fluoro-D-glucopyranoside dissolved in <1 ml saline is injected intravenously, and the distribution of the tracer is followed dynamically in whole body PET scans for up to 2 hours (up to 8 scans at different time intervals). SGLT activity in organs and tissues is determined from the tracer uptake. The anatomical location of tracer uptake in both normal subjects and cancer patients is determined using CT scans.

Figure 4:
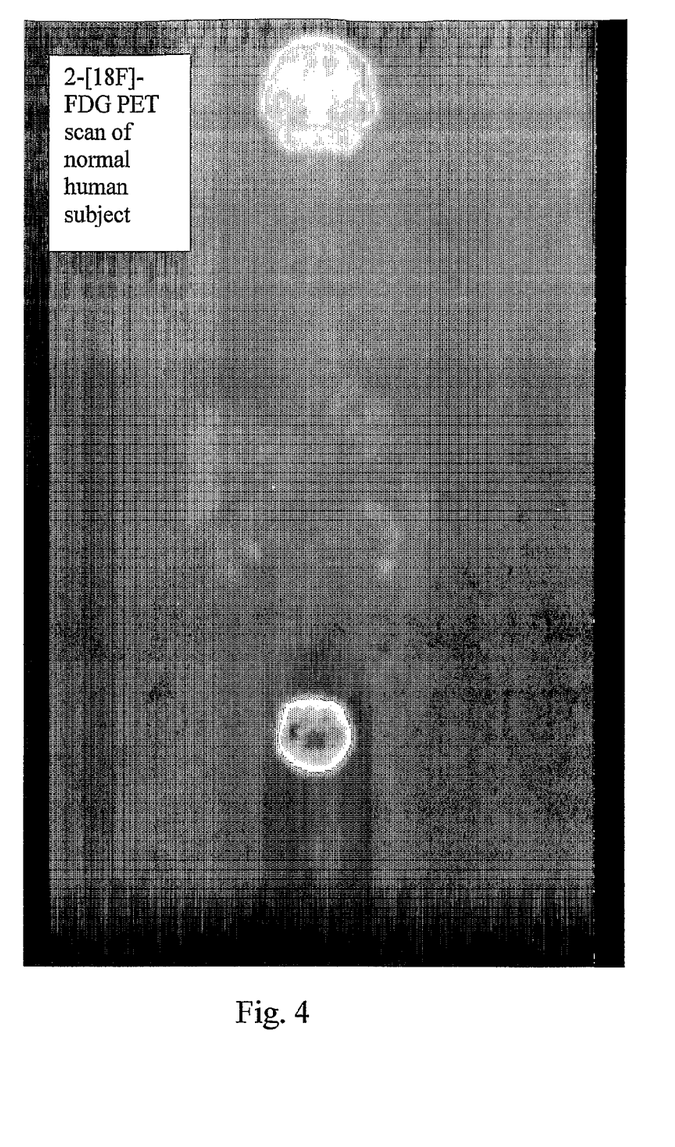
FIG. 4 is a 2-[$^{18}$F]-FDG PET scan of a normal human subject.
Figure 5:
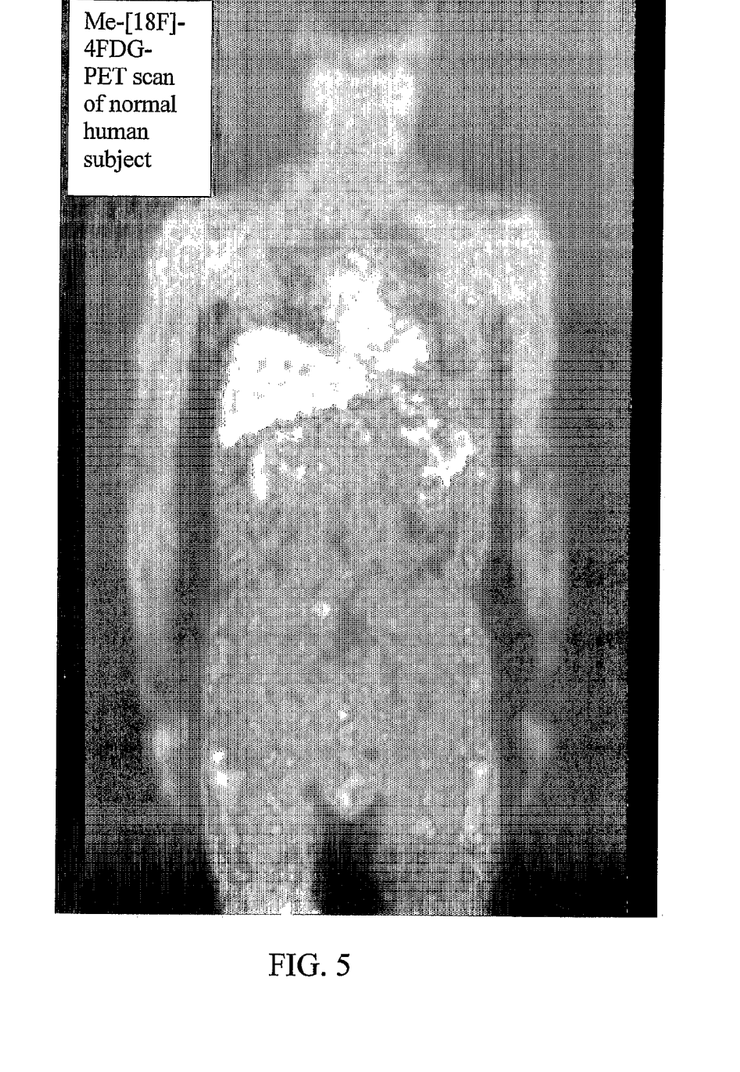
FIG. 5 is a Me-4-[$^{18}$F]-FDG PET scan of a normal human subject.

FIGS. 4 and 5 are nonlimiting examples of 2-[$^{18}$F]-FDG and Methyl 4[$^{18}$F]-FDG scans, respectively, of the same human subject. Note that the tracer 2-[$^{18}$F]-FDG is accumulated in the brain and eliminated into the urinary bladder, whereas Methyl 4[$^{18}$F]-FDG is not.

To differentiate between the activity of SGLT1 and SGLT2, PET scans are also conducted with methyl 4-deoxy-4-[$^{18}$F] fluoro-beta-D-galactopyranoside, which is a substrate for SGLT1 but not SGLT2. A bolus of the radiolabeled galactopyranoside tracer is administered to the human subject intravenously or orally, and the tracer's uptake into organs and tissues is followed by PET scans. Whole body scans are again conducted for up to 2 hours, and the activity of SGLTs is monitored by the uptake of the tracer into each organ and tissue. The kinetics of tracer uptake by SGLTs is determined by standard modeling methods (see for example, Carson R. E. Tracer Kinetic Modeling. In: Valk P. E. et al. Positron Emission Tomography, Springer, 2003). The role of SGLT1 and SGLT2 tracer uptakes into specific organs and tissues will also be determined by conducting scans on patients with known defects in SGLT1 (Glucose-Galactose-Malabsorption) or SGLT2 (renal glucosuria). Similar studies with Methyl-D-mannopyranoside tracers enables one to dissect out the role of SGLT4 vs. SGLT1 and SGLT2 in sugar uptake into specific organs and tissues.

Figure 6:
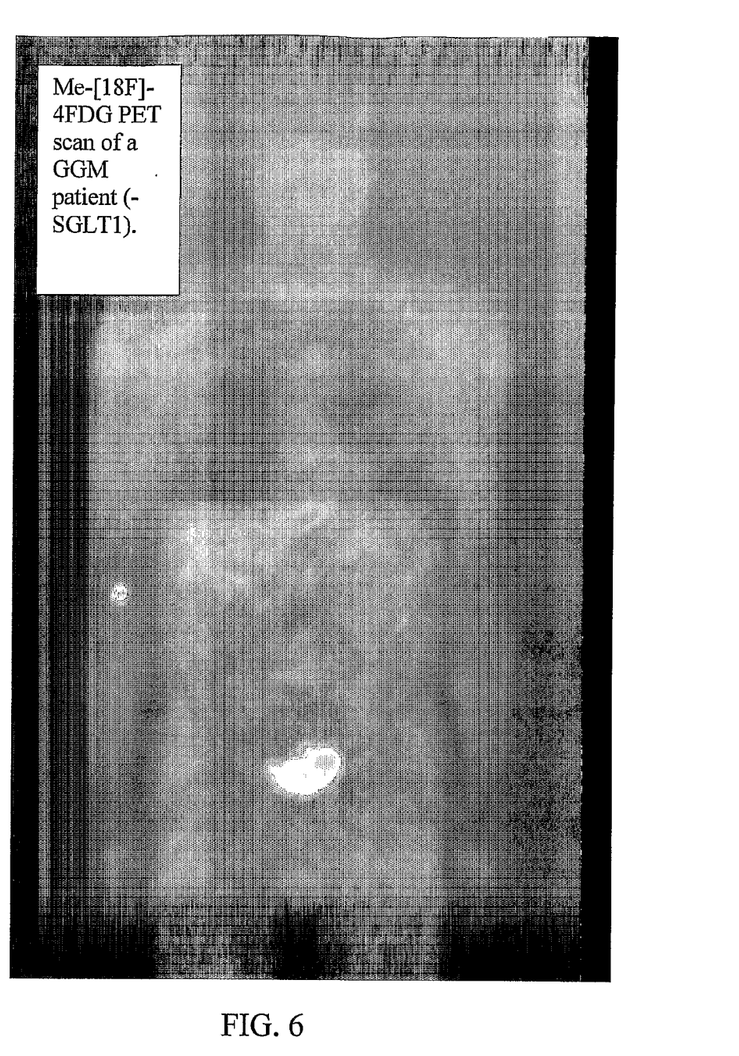
FIG. 6 is a Me-4-[$^{18}$F]-FDG PET scan of a human subject missing functional SGLT1 transporters.

FIG. 6 is a nonlimiting example of a whole body PET scan of a patient with Glucose-Galactose-Malabsorption (missing functional SGLT1 in his body), after being injected with Me-[18F]-4FDG. Note the excretion of the tracer into the urinary bladder.

Example 6

Use of a Tracer for In Vivo Monitoring of a Therapeutic Intervention

A radiolabeled tracer is injected intravenously or orally administered to a human or other mammal, and whole body PET scans are recorded for up to 2 hours. The effect of a therapeutic drug (e.g. phlorizin) or drug candidate, on renal glucose excretion is monitored by the appearance of the tracer in the bladder, and the effect of the drug on tracer uptake into other organs and tissues is monitored simultaneously. The drug is administered intravenously, orally, or by some other suitable mode of delivery, at various times before and after the start of the PET scan. In this manner, the time, dosage, and route of administration of the drug on renal glucose excretion and uptake into other organs and tissues is precisely determined.

Additional Findings and Examples

Blood-Brain-Barrier Permeable SGLT PET Probes are Substrates for SGLTs

Hexoses with an equatorial hydroxyl group on carbon #2, e.g. D-glucose and D-galactose, are capable of crossing the blood-brain barrier. According to another aspect of the invention, radiohalogenated analogs of such compounds, e.g., compounds of types L-Q in Table 1, are used to probe SGLT activity in the brain of a human or non-human mammal. Halogenated hexoses such as 4-[$^{18}$F]fluoro-4-deoxy-D-glucose and 4-[$^{18}$F]fluoro-4-deoxy-D-galactose are high affinity substrates (competitive inhibitors) for human GLUT1, the blood brain barrier glucose transporter (see Barnett et al.

Biochem J. 131: 211-221, 1973). In particular, the inhibitor constants for sugar uptakes into human erythrocytes were ~7 mM for D-glucose, 3-deoxy-3-fluoro-D-glucose, and 6-deoxy-6-fluoro-D-galactose, and 1.3 mM for 6-deoxy-6-fluoro-D-glucose. There are reports on 6-[$^{18}$F]fluoro-6-deoxy-D-glucose suggesting that this probe is transported into cultured cells expressing GLUT transporters (Neal, T R et al. J Label Compd Radiopharm 2005; 48:845-854, 2005). In preliminary microPET studies we have established that such substrates, e.g. 4-[$^{18}$F]fluoro-4-deoxy-D-glucose, are taken up rapidly into rodent brains.

We have expressed human SGLT1 in the *Xenopus laevis* oocyte expression system and measured the kinetics of halogenated hexose transport using standard electrophysiological assays (see Diez-Sampedro et al. J. Biological Chemistry, 2001, 276: 49188-49194). Table 2 presents kinetic measurements of the SGLT1 affinities of various sugars. The GLUT1 and hexolinase data were obtained from Barnett et al. Biochem J. 131: 211-221 (1973) and Bessel, E. M. Biochem J. 128:199-204, 1972), respectively, and are provided for comparison. "$K_m$" is the Michaelis-Menten constant and refers to the ability of a sugar to be a substrate for a specific enzyme or transporter. The lower the $K_m$, the better the substrate. "$V_{max}$" refers to the maximum velocity of transport (or enzymatic reaction). $K_m$ is the concentration of substrate at ½ $V_{max}$. "$K_i$" is an inhibition constant for a specific enzyme or transporter, obtained by competitive kinetics against a known substrate.

TABLE 2

Sugar-Metabolic Transport Affinities

| Sugar | SGLT1 $K_m$ (mM) | GLUT1* $K_i$ (mM) | Hexokinase** $K_i$ (mM) | $V_{max}$ |
|---|---|---|---|---|
| D-glucose | 0.5 | 6 | 0.2 | 1 |
| D-galactose | 0.6 | 90 | n.d. | n.d. |
| 1-F-1-deoxy-D-glucose | 0.5 | 15 | n.d. | n.d. |
| 2-F-2-deoxy-D-glucose | >100 | 3.6 | 0.2 | 0.5 |
| 3-F-3-deoxy-D-glucose | 5 | 7 | 70 | 0.1 |
| 4-F-4-deoxy-D-glucose | 0.07 | n.d. | 84 | 0.1 |
| 4-F-4-deoxy-D-galactose | 1.3 | n.d. | n.d. | n.d. |
| 6-F-4-deoxy-D-glucose | 3 | 1 | 0 | 0 | n.d. Not reported
*Barnett et al. (1973)
**Bessel (1972)

The data summarized in Table 2 show that all fluoro-hexoses are good substrates for SGLT1, and several interact with GLUT1 with similar affinities to that of D-glucose.

Differentiating Between Uptakes Due to SGLTs and GLUTs

1. Compare and Contrast Biodistribution of 2-FDG and SGLT Probes.

(a) Uptakes of 2-FDG are limited to those by GLUTs, as 2-FDG is a good substrate for GLUTs but not SGLTs (Table 2).

(b) Accumulation of 2-FDG in GLUT-expressing cells occurs through the metabolic sink action of hexolinase, i.e. conversion of 2-FDG to 2-FDG-6-phosphate, which is not a substrate for GLUTs.

1-FDG, 3-FDG, 4-FDG, 6-FDG, and the respective galactose derivatives are poor substrates for hexokinase, e.g. the 3-FDG and 4-FDG affinities are 400-fold lower and the maximum velocities are 10-fold lower than those for D-glucose (Table 2). Thus these hexose probes should not be accumulated in cells expressing GLUTs owing to the low predicted rate of metabolic conversion to their corresponding 6-phosphates that are accumulated in cells (e.g., charged phosphate derivatives that do not cross cell membranes).

(c) In cells expressing SGLTs, PET probes such as 3-FDG, 4-FDG, 6-FDG, and the respective galactose analogs will be accumulated by Na/sugar cotransporters. The maximum intracellular concentration is determined by the extra- and intra-cellular Na concentrations, $[Na]_e$ and $[Na]_i$, and the membrane potential $E_m$ (mV) is determined from the relationship:

$$[S]_i/[S]_e = \{[Na]_e/[Na]_i\} \exp 2(E_m/25)$$

where $[S]_i$ and $[S]_e$ are the intracellular and extracellular sugar concentrations, respectively. Therefore, in the case of hexose probes with low rates of metabolic conversion (e.g., to hexose-6-phosphate), accumulation will only be observed in tissues expressing SGLTs, as a result of the functionally irreversible characteristics of SGLTs (e.g., unidirectional transport of glucose or substrate analogs).

The invention has been described with reference to various embodiments and examples, but is not limited thereto. Variations may be made without departing from the invention's scope, which is limited only by the appended claims, which are to be afforded their full scope, both literally and by equivalents. The invention is limited only by the appended claims and their equivalents.

Each of the above references is incorporated herein as if set forth in its entirety.

What is claimed is:

1. A tracer compound specific for a sodium/glucose cotransporter (SGLT), comprising a material selected from the group consisting of radiolabeled, C 1 methyl pyranosides having an equatorial hydroxyl group at carbon-2; radiolabeled C 1 ethyl pyranosides having an equatorial hydroxyl group at carbon-2; radiolabeled hexoses having an equatorial hydroxyl group at carbon-2; $^{11}$C-labeled analogs of C 1-O-methyl pyranosides bearing a $^{11}$C methyl group at carbon-1, 3, 4, or 6, and having an equatorial hydroxyl group at carbon-2; $^{11}$C-labeled analogs of C 1-O-methyl-halo-deoxy-pyranosides bearing a $^{11}$C methyl group at carbon-1, 3, 4, or 6, and having an equatorial hydroxyl group at carbon-2; and mixtures thereof, the tracer compound configured to specifically bind a SGLT, wherein:

the radiolabeled, C 1 methyl pyranosides having an equatorial hydroxyl group at carbon-2 is selected from the group consisting of:

C 1-O-methyl 3-deoxy-3-[$^{18}$F]fluoro-D-glucopyranosides,

C 1-O-methyl 4-deoxy-4-[$^{18}$F]fluoro-D-glucopyranosides,

C 1-O-methyl 6-deoxy-6-[$^{18}$F]fluoro-D-glucopyranosides,

C 1-O-methyl 3-deoxy-3-[$^{18}$F]fluoro-D-galactopyranosides,

C 1-O-methyl 4-deoxy-4-[$^{18}$F]fluoro-D-galactopyranosides,

C 1-O-methyl 6-deoxy-6-[$^{18}$F]fluoro-D-galactopyranosides,

C 1-O-methyl-3-deoxy-3-[$^{18}$F]fluoro-D-mannopyranosides,

C 1-O-methyl 4-deoxy-4-[$^{18}$F]fluoro-D-mannopyranosides,

C 1-O-methyl 6-deoxy-6-[$^{18}$F]fluoro-D-mannopyranosides,

C 1-O-methyl 3-deoxy-3-[$^{123}$I]iodo-D-glucopyranosides,

C 1-O-methyl 4-deoxy-4-[$^{123}$I]iodo-D-glucopyranosides,
C 1-O-methyl 6-deoxy-6-[$^{123}$I]iodo-D-glucopyranosides,
C 1-O-methyl 3-deoxy-3-[$^{123}$I]iodo-D-galactopyranosides,
C 1-O-methyl 4-deoxy-4-[$^{123}$I]iodo-D-galactopyranosides,
C 1-O-methyl 6-deoxy-6-[$^{123}$I]iodo-D-galactopyranosides,
C 1-O-methyl 3-deoxy-3-[$^{123}$I]iodo-D-mannopyranosides,
C 1-O-methyl 4-deoxy-4-[$^{123}$I]iodo-D-mannopyranosides,
C 1-O-methyl 6-deoxy-6-[$^{123}$I]iodo-D-mannopyranosides,
C 1-O-methyl 3-deoxy-3-[$^{124}$I]iodo-D-glucopyranosides,
C 1-O-methyl 4-deoxy-4-[$^{124}$I]iodo-D-glucopyranosides,
C 1-O-methyl 6-deoxy-6-[$^{124}$I]iodo-D-glucopyranosides,
C 1-O-methyl 3-deoxy-3-[$^{124}$I]iodo-D-galactopyranosides,
C 1-O-methyl 4-deoxy-4-[$^{124}$I]iodo-D-galactopyranosides,
C 1-O-methyl 6-deoxy-6-[$^{124}$I]iodo-D-galactopyranosides,
C 1-O-methyl 3-deoxy-3-[$^{124}$I]iodo-D-mannopyranosides,
C 1-O-methyl 4-deoxy-4-[$^{124}$I]iodo-D-mannopyranosides,
C 1-O-methyl 6-deoxy-6-[$^{124}$I]iodo-D-mannopyranosides,
C 1-O-[$^{123}$I]iodomethyl-D-glucopyranosides,
C 1-O-[$^{124}$I]iodomethyl-D-glucopyranosides,
C 1-O-[$^{123}$I]iodomethyl-D-galactopyranosides,
C 1-O-[$^{124}$I]iodomethyl-D-galactopyranosides,
C 1-O-[$^{123}$I]iodomethyl-D-mannopyranosides, and
C 1-O-[$^{124}$I]iodomethyl-D-mannopyranosides, the radiolabeled, C 1 ethyl pyranosides having an equatorial hydroxyl group at carbon-2 is selected from the group consisting of:
C 1-O-ethyl 3-deoxy-3-[$^{18}$F]fluoro-D-glucopyranosides,
C 1-O-ethyl 4-deoxy-4-[$^{18}$F]fluoro-D-glucopyranosides,
C 1-O-ethyl 6-deoxy-6-[$^{18}$F]fluoro-D-glucopyranosides,
C 1-O-ethyl 3-deoxy-3-[$^{18}$F]fluoro-D-galactopyranosides,
C 1-O-ethyl 4-deoxy-4-[$^{18}$F]fluoro-D-galactopyranosides,
C 1-O-ethyl 6-deoxy-6-[$^{18}$F]fluoro-D-galactopyranosides,
C 1-O-ethyl 3-deoxy-3-[$^{18}$F]fluoro-D-mannopyranosides,
C 1-O-ethyl 4-deoxy-4-[$^{18}$F]fluoro-D-mannopyranosides,
C 1-O-ethyl 6-deoxy-6-[$^{18}$F]fluoro-D-mannopyranosides,
C 1-O-ethyl 3-deoxy-3-[$^{123}$I]iodo-D-glucopyranosides,
C 1-O-ethyl 4-deoxy-4-[$^{123}$I]iodo-D-glucopyranosides,
C 1-O-ethyl 6-deoxy-6-[$^{123}$I]iodo-D-glucopyranosides,
C 1-O-ethyl 3-deoxy-3-[$^{123}$I]iodo-D-galactopyranosides,
C 1-O-ethyl 4-deoxy-4-[$^{123}$I]iodo-D-galactopyranosides,
C 1-O-ethyl 6-deoxy-6-[$^{123}$I]iodo-D-galactopyranosides,
C 1-O-ethyl 3-deoxy-3-[$^{123}$I]iodo-D-mannopyranosides,
C 1-O-ethyl 4-deoxy-4-[$^{123}$I]iodo-D-mannopyranosides,
C 1-O-ethyl 6-deoxy-6-[$^{123}$I]iodo-D-mannopyranosides,
C 1-O-ethyl 3-deoxy-3-[$^{124}$I]iodo-D-glucopyranosides,
C 1-O-ethyl 4-deoxy-4-[$^{124}$I]iodo-D-glucopyranosides,
C 1-O-ethyl 6-deoxy-6-[$^{124}$I]iodo-D-glucopyranosides,
C 1-O-ethyl 3-deoxy-3-[$^{124}$I]iodo-D-galactopyranosides,
C 1-O-ethyl 4-deoxy-4-[$^{124}$I]iodo-D-galactopyranosides,
C 1-O-ethyl 6-deoxy-6-[$^{124}$I]iodo-D-galactopyranosides,
C 1-O-ethyl 3-deoxy-3-[$^{124}$I]iodo-D-mannopyranosides,
C 1-O-ethyl 4-deoxy-4-[$^{124}$I]iodo-D-mannopyranosides,
C 1-O-ethyl 6-deoxy-6-[$^{124}$I]iodo-D-mannopyranosides,
C 1-O-1-[$^{123}$I]iodoethyl-D-galactopyranosides,
C 1-O-2-[$^{123}$I]iodoethyl-D-galactopyranosides,
C 1-O-1-[$^{124}$I]iodoethyl-D-galactopyranosides,
C 1-O-2-[$^{124}$I]iodoethyl-D-galactopyranosides,
C 1-O-1-[$^{123}$I]iodoethyl-D-mannopyranosides,
C 1-O-2-[$^{123}$I]iodoethyl-D-mannopyranosides,
C 1-O-1-[$^{124}$I]iodoethyl-D-mannopyranosides, and
C 1-O-2-[$^{124}$I]iodoethyl-D-mannopyranosides;

the radiolabeled hexoses having an equatorial hydroxyl group at carbon-2 is selected from the group consisting of:
1-[$^{18}$F]fluoro-1-deoxy-D-glucose
6-[$^{18}$F]fluoro-6-deoxy-D-glucose
1-[$^{18}$F]fluoro-1-deoxy-D-galactose
3-[$^{18}$F]fluoro-3-deoxy-D-galactose
4-[$^{18}$F]fluoro-4-deoxy-D-galactose
6-[$^{18}$F]fluoro-6-deoxy-D-galactose
1-[$^{123}$I]iodo-1-deoxy-D-glucose
3-[$^{123}$I]iodo-3-deoxy-D-glucose
4-[$^{123}$I]iodo-4-deoxy-D-glucose
6-[$^{123}$I]iodo-6-deoxy-D-glucose
1-[$^{123}$I]iodo-1-deoxy-D-galactose
3-[$^{123}$I]iodo-3-deoxy-D-galactose
4-[$^{123}$I]iodo-4-deoxy-D-galactose
6-[$^{123}$I]iodo-6-deoxy-D-galactose
1-[$^{124}$I]iodo-1-deoxy-D-galactose
3-[$^{124}$I]iodo-3-deoxy-D-galactose
4-[$^{124}$I]iodo-4-deoxy-D-galactose
6-[$^{124}$I]iodo-6-deoxy-D-galactose
1-[$^{124}$I]iodo-1-deoxy-D-galactose
3-[$^{124}$I]iodo-3-deoxy-D-galactose
4-[$^{124}$I]iodo-4-deoxy-D-galactose
6-[$^{124}$I]iodo-6-deoxy-D-galactose
1-[$^{18}$F]fluoro-1-deoxy-D-mannose
3-[$^{18}$F]fluoro-3-deoxy-D-mannose
4-[$^{18}$F]fluoro-4-deoxy-D-mannose
6-[$^{18}$F]fluoro-6-deoxy-D-mannose 1-[$^{123}$I]iodo-1-deoxy-D-mannose
3-[$^{123}$I]iodo-3-deoxy-D-mannose
4-[$^{123}$I]iodo-4-deoxy-D-mannose
6-[$^{123}$I]iodo-6-deoxy-D-mannose
1-[$^{124}$I]iodo-1-deoxy-D-mannose
3-[$^{124}$I]iodo-3-deoxy-D-mannose
4-[$^{124}$I]iodo-4-deoxy-D-mannose
6-[$^{124}$I]iodo-6-deoxy-D-mannose.

2. The tracer compound as recited in claim 1, wherein the radiolabeled, methyl pyranosides or ethyl pyranosides comprise methyl 4-deoxy-4-[$^{18}$F]fluoro-alpha-D-glucopyranoside.

3. The tracer compound as recited in claim 1, wherein the radiolabeled, methyl pyranosides or ethyl pyranosides comprise methyl 4-deoxy-4-[$^{18}$F]fluoro-beta-D-glucopyranoside.

4. The tracer compound as recited in claim 1, wherein the radiolabeled, methyl pyranosides or ethyl pyranosides comprise a racemic mixture of methyl 4-deoxy-4-[$^{18}$F]fluoro-alpha-D-glucopyranoside and methyl 4-deoxy-4-[$^{18}$F]fluoro-beta-D-glucopyranoside.

5. A method of detecting a sodium/glucose cotransporter (SGLT) in vitro, comprising:
obtaining a cellular sample;
administering to the cellular sample a radiolabeled tracer;
after a first predetermined time interval, isolating a first aliquot of the cellular sample;
assaying the first aliquot for radioactivity; and
after each of one or more additional predetermined time intervals, isolating a further aliquot of the cellular sample and assaying it for radioactivity;
wherein the radiolabeled tracer compound comprises at least one of the tracer compounds recited in claim 1.

6. The method as recited in claim 5, wherein the cellular sample is selected from the group consisting of a single mammalian cell, a plurality of mammalian cells, a mammalian tissue sample, and mixtures thereof.

7. The method as recited in claim 5, wherein the tracer compound comprises methyl 4-deoxy-4-[$^{18}$F]fluoro-D-glucopyranoside.

8. The method as recited in claim 5, further comprising administering to the cellular sample at least one agent.

9. The method as recited in claim 8, wherein the at least one agent is selected from the group consisting of sodium ion, phlorizin, glucose, and galactose.

10. The method as recited in claim 5, further comprising washing the first and each subsequent aliquot of the cellular sample with a buffer solution.

11. A method of assessing sodium/glucose cotransporter (SGLT) distribution or activity in a mammal, in vivo, comprising:
administering to the mammal a bolus of a radiolabeled tracer;
generating radiographic data indicative of tracer uptake in the mammal by scanning the mammal using a radiographic technique; and
using the radiographic data to assess SGLT distribution or activity in the mammal;
wherein the radiolabeled tracer comprises at least one of the tracer compounds recited in claim 1.

12. The method as recited in claim 11, wherein the mammal is selected from the group consisting of humans, non-human primates, rodents, wild-type rodents, transgenic rodents and knockout rodents.

13. The method as recited in claim 11, wherein the radiographic technique comprises autoradiography, scintillation counting, positron emission tomography (PET), micro-PET, or single-photon emission computed tomography (SPECT).

14. The method as recited in claim 11, further comprising administering to the mammal at least one agent.

15. The method as recited in claim 14, wherein the at least one agent is selected from the group consisting of sodium ion, phlorizin, glucose, and galactose.

16. The method as recited in claim 14, wherein the at least one agent is administered orally or by injection.

17. The method as recited in claim 11, further comprising locating uptake of the tracer compound in the mammal using computed tomography.

18. A method of monitoring sodium/glucose cotransporter activity in a mammal, in vivo, comprising:
administering to a mammal a bolus of a radiolabeled tracer known to be a substrate for a first specified sodium/glucose cotransporter, but not a substrate for a second specified sodium/glucose cotransporter;
generating radiographic data indicative of tracer uptake in the mammal by scanning the mammal using a radiographic technique; and
using the radiographic data to assess distribution or activity of the first specified sodium/glucose cotransporter in the mammal;
wherein the radiolabeled tracer comprises at least one of the tracer compounds recited in claim 1.

19. The method as recited in claim 18, wherein the radiographic technique comprises one or more computed tomographic scans of all or part of the mammal's body.

20. A method of evaluating therapeutic effect of an agent on a sodium/glucose cotransporter in a mammal, comprising:
A
administering a radiolabeled tracer to a mammal;
generating a first set of radiographic data by scanning the mammal using a radiographic technique;
administering an actual or proposed therapeutic agent to the mammal, intravenously, orally, or by other suitable mode of delivery;
generating a second set of radiographic data by scanning the mammal using a radiographic technique; and
comparing the first and second sets of radiographic data; or
B
administering an actual or proposed therapeutic agent to the mammal, intravenously, orally, or by other suitable mode of delivery;
administering to the mammal a radiolabeled tracer to the mammal;
generating a set of radiographic data by scanning the mammal using a radiographic technique; and
comparing the set of radiographic data to data obtained in the absence of the agent;
wherein in A and B the radiolabeled tracer comprises at least one compound selected from the group consisting of (a) any of the tracers recited in claim 1.

21. A method of making a methyl 4-deoxy-4-[$^{18}$F]fluoro-D-glucopyranoside, comprising:
forming a methyl 2,3,6-tri-O-acetyl-4-deoxy-[$^{18}$F]fluoro-D-glucopyranoside by heating a methyl 2,3,6-tri-O-acetyl-4-trifyl-D-galactopyranoside in the presence of [$^{18}$F]fluoride ion; and
deacetylating the methyl 2,3,6-tri-O-acetyl-4-deoxy-[$^{18}$F]fluoro-D-glucopyranoside with acid to yield a methyl 4-deoxy-4-[$^{18}$F]fluoro-D-glucopyranoside.

22. A method as recited in claim 21, wherein the methyl 2,3,6-tri-O-acetyl-4-trifyl-D-galactopyranoside is methyl 2,3,6-tri-O-acetyl-4-trifyl-beta-D-galactopyranoside, and the methyl 4-deoxy-4-[$^{18}$F]fluoro-D-glucopyranoside is methyl 4-deoxy-4-[$^{18}$F]fluoro-beta-D-glucopyranoside.

23. A method of monitoring sodium/glucose cotransporter activity in a mammal's brain, in vivo, comprising:
   administering to a mammal a bolus of a radiolabeled tracer of claim 1 for a sodium/glucose cotransporter and capable of crossing the mammal's blood-brain barrier; and
   generating radiographic data indicative of tracer uptake in the mammal's brain by scanning the brain using a radiographic technique, in vivo.

24. A method as recited in claim 23, wherein the radiolabeled tracer comprises a radiolabeled hexose as recited in claim 1.

25. A method as recited in claim 23, wherein the mammal's brain is healthy.

26. A method as recited in claim 23, wherein the mammal is suffering from Alzheimer's disease, Parkinson's disease, non-Alzheimer's-type dementia, epilepsy, stroke, brain tumor, or brain injury.

27. The composition of claim 1, wherein the tracer compound is selected from the group consisting of radiolabeled, C 1 methyl pyranosides having an equatorial hydroxyl group at carbon-2; radiolabeled C 1 ethyl pyranosides having an equatorial hydroxyl group at carbon-2; $^{11}$C-labeled analogs of C 1-O-methyl pyranosides bearing a $^{11}$C methyl group at carbon-1, 3, 4, or 6, and having an equatorial hydroxyl group at carbon-2; $^{11}$C-labeled analogs of C 1-O-methyl-halo-deoxy-pyranosides bearing a $^{11}$C methyl group at carbon-1, 3, 4, or 6, and having an equatorial hydroxyl group at carbon-2; and mixtures thereof.

* * * * *